United States Patent
Zydowicz et al.

(10) Patent No.: US 10,729,799 B2
(45) Date of Patent: Aug. 4, 2020

(54) AQUEOUS HYDROGEN PEROXIDE SOLUTION COMPRISING A SPECIFIC STABILIZER

(71) Applicant: Arkema France, Colombes (FR)

(72) Inventors: Philippe Zydowicz, Saint Priest (FR); Pierre Larnicol, Verriere le Buisson (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 15/776,526

(22) PCT Filed: Nov. 18, 2016

(86) PCT No.: PCT/FR2016/053016
§ 371 (c)(1),
(2) Date: May 16, 2018

(87) PCT Pub. No.: WO2017/085428
PCT Pub. Date: May 26, 2017

(65) Prior Publication Data
US 2018/0326106 A1 Nov. 15, 2018

(30) Foreign Application Priority Data
Nov. 18, 2015 (FR) ........................ 15 61086

(51) Int. Cl.
| | | |
|---|---|---|
| *A61L 2/22* | (2006.01) | |
| *C01B 15/037* | (2006.01) | |
| *A61L 2/18* | (2006.01) | |
| *A01N 59/00* | (2006.01) | |
| *A61L 2/20* | (2006.01) | |

(52) U.S. Cl.
CPC .............. *A61L 2/22* (2013.01); *A01N 59/00* (2013.01); *A61L 2/186* (2013.01); *A61L 2/208* (2013.01); *C01B 15/037* (2013.01)

(58) Field of Classification Search
CPC . A61L 2/22; A61L 2/208; A61L 2/186; A01N 59/00; A01N 25/22; C01B 15/037
See application file for complete search history.

(56) References Cited

U.S. PATENT DOCUMENTS

| | | | |
|---|---|---|---|
| 5,759,440 A | 6/1998 | Van Hemelrijk | |
| 6,323,169 B1 * | 11/2001 | Abe | ......... C11D 3/33 510/176 |
| 2002/0182103 A1 * | 12/2002 | Biering | ........ A01N 37/16 422/28 |
| 2011/0052445 A1 | 3/2011 | Herdt et al. | |
| 2011/0123642 A1 * | 5/2011 | Wilmotte | ........ A01N 59/00 424/616 |
| 2012/0164236 A1 * | 6/2012 | Iwasa | ........ A01N 59/16 424/616 |
| 2012/0288570 A1 * | 11/2012 | Zhu | ......... D06L 4/12 424/616 |

FOREIGN PATENT DOCUMENTS

| | | | | |
|---|---|---|---|---|
| CN | 102256713 A | 11/2011 | | |
| EP | 1762252 A1 * | 3/2007 | ........... | A01N 59/00 |
| EP | 1762252 A1 | 3/2007 | | |
| EP | 1926502 B1 | 2/2011 | | |
| EP | 2338961 A1 | 6/2011 | | |
| WO | WO2010004161 A2 | 1/2010 | | |
| WO | WO-2010073976 A1 * | 7/2010 | ........... | B09C 1/002 |
| WO | WO2013026971 A1 | 2/2013 | | |
| WO | WO2015/078830 A1 | 6/2015 | | |
| WO | WO2016082897 A1 | 6/2016 | | |

OTHER PUBLICATIONS

ISA/EP, International Search Report and Written Opinion for PCT Patent Application No. PCT/FR2016/053016, dated Feb. 23, 2017.

* cited by examiner

Primary Examiner — Pamela H Weiss
(74) Attorney, Agent, or Firm — NK Patent Law

(57) ABSTRACT

An aqueous hydrogen peroxide solution comprises a stabilizer chosen from the family of substituted or unsubstituted aminopolycarboxylic acids (APCA) or salts thereof. The solution may be used for disinfecting a packaging.

10 Claims, No Drawings

AQUEOUS HYDROGEN PEROXIDE SOLUTION COMPRISING A SPECIFIC STABILIZER

CROSS REFERENCE TO RELATED APPLICATIONS

This application is a U.S. National Stage application of International Application No. PCT/FR2016/053016 filed on Nov. 18, 2016, which claims the benefit of French Patent Application No. 1561086 filed on Nov. 18, 2015, the entire content of all of which is incorporated by reference herein.

FIELD OF THE INVENTION

The present invention relates to an aqueous hydrogen peroxide solution comprising a specific stabilizer which allows it to obtain significantly improved properties compared with the products of the prior art.

The invention also relates to a disinfection or even a sterilization process, using the aqueous solution according to the present invention. Finally, a subject of the invention is the use of such a specifically stabilized aqueous disinfecting solution for disinfecting a packaging.

TECHNICAL BACKGROUND

To disinfect or sterilize a packaging, a disinfection or sterilization technique consists in spraying said packaging using a spray of an aqueous hydrogen peroxide solution. With this solution, a certain amount of stabilizer(s) is necessary, which leads to the presence, in the hydrogen peroxide solution, of residues originating from the decomposition or from the presence of the stabilizers (besides those originating from the hydrogen peroxide).

Stabilizers are essential for the aqueous hydrogen peroxide solution, since they prevent the degradation of hydrogen peroxide (exothermic dismutation reaction into water and oxygen). This need for a stabilizer is all the more profound the more the hydrogen peroxide content increases. Thus, in order for hydrogen peroxide solution is to be efficient in disinfection or sterilization, the hydrogen peroxide content must be high, and consequently the stabilizer content also.

However, the residues resulting from these stabilizers may block the nozzle(s) and pipes of the spraying apparatus (spraying).

Needless to say, it is possible to clean the spraying apparatus, but this entails stoppage of the disinfecting/sterilizing device and also non-negligible additional costs, besides the fact that the sprayer may be irreparably damaged. Only solutions having very low contents of residues would thus allow the use of such aqueous hydrogen peroxide solutions by spraying.

Documents are known at the present time, which propose novel types of stabilizers, such as in EP 1926502 or WO 2015/078830, but none of these solutions makes it possible to achieve an extremely low level of residues that is essential for use by spraying.

Thus, there is a need for an efficient disinfecting/sterilizing solution, which is stable over time (conservation of the hydrogen peroxide titer) and which has a very low content of residues.

SUMMARY OF THE INVENTION

The object of the present invention is to overcome the abovementioned drawbacks. To this end, the invention proposes the use of stabilizers of a quite specific chemical family, which, whilst ideally fulfilling their first function (stabilization of hydrogen peroxide), can ensure a particularly low level of residues, such that the operations for disinfection/sterilization of a packaging do not entail any risk of damage, even in the very long term, to the appliances required for these operations (without moreover requiring washing/cleaning operations).

The disinfecting/sterilizing composition according to the invention ensures, in a particularly surprising manner, the stability of hydrogen peroxide (active principle of the composition) at room temperature even in the presence of a small metallic contamination. The stability results for the composition according to the invention show a very significant improvement in the stability properties, while at the same time offering a very small amount of residues that are liable to deteriorate the devices used for dispensing (projection, spraying, nebulization, vaporization, etc.) the hydrogen peroxide composition. Surprisingly, such stability is observed even for large contents of hydrogen peroxide, such as those required to ensure efficient this infection/sterilization.

In addition, the disinfecting/sterilizing composition according to the invention allows the disinfection of packaging intended for packaging human or animal food, cosmetic products and pharmaceutical or veterinary products.

Thus, the present invention relates to an aqueous hydrogen peroxide solution comprising from 1% to 98%, in particular from 3% to 75%, preferably from 20 to 98%, preferably from 20 to 75%, preferably from 20% to 65%, preferably from 20 to 50% and more preferentially from 22% to 38% by weight of the solution, of hydrogen peroxide and from 0.01 to 7 mg/kg (milligrams per kilogram), preferably from 0.5 to 7 mg/kg and more preferentially from 1.5 to 5 mg/kg, by weight of the solution, of a stabilizer, characterized in that the stabilizer is chosen from the family substituted or unsubstituted of aminopolycarboxylic acids (APCA) or salts thereof, of general formula:

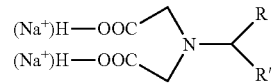

in which R and R' are chosen from the following functional groups:
C1 to C3 alkyls, preferably a methyl group,
C1 to C3 carboxylic acids.

It is clearly understood that the amount of stabilizers indicated above relates to an amount of active material of the stabilizer(s), the latter possibly being available, optionally commercially, in the form of a solution diluted in water.

The present invention finds an application in particular for any use of the aqueous solution according to the invention in vaporized form, especially such as in the application known as an "aseptic spray" known to those skilled in the art, and more generally for disinfection/sterilization via vaporization of the hydrogen peroxide solution.

In the text hereinbelow, unless otherwise mentioned, the percentages are given as mass values.

It is clearly understood that the term "stabilizer" refers the present patent application to any component whose function is to ensure the stability over time of the hydrogen peroxide present in the aqueous solution so that it undergoes little or no decomposition and so that the solution remains substantially identical over time, for example on storage. As non-limiting examples of such stabilizers used in the prior art, mention may be made of phosphonic acids and salts thereof, such as aminotris(methylenephosphonic acid), hydroxyethylenediphosphonic acid or diethylenetriaminepentamethylphosphonic acid, polyphosphates, pyrophosphates such as sodium hydrogen pyrophosphate, phosphoric acid and salts thereof, sodium stannate, carboxylic acids and ethylenediaminetetraacetic acid derivatives.

For the purposes of the invention, the "disinfection" of a packaging may be understood as extending from a partial destruction of the microorganisms present on the surface of the packaging so as to slow down their illustrations, to virtually total extermination of said microorganisms, depending on the intended application. In the latter case, this is generally referred to as "sterilization". The aqueous hydrogen peroxide composition according to the invention is suitable for these two uses.

In order to ensure adequate disinfection/sterilization, a minimum content of 20% and preferably 22% of hydrogen peroxide relative to the total weight of the composition is required.

Preferably, the solution according to the present invention comprises from 20 to 98%, preferably from 20 to 75%, preferably from 20% to 65%, preferably from 20 to 50% and more preferentially from 22% to 38% of hydrogen peroxide relative to the total weight of the composition.

A hydrogen peroxide content of from 22% to 38% relative to the total weight of the composition is particularly suitable for the disinfection/sterilization of packagings.

The terms "residue(s)", "dry residue(s)" and "dry evaporation residues" of the solution according to the present invention means the solid matter collected after evaporation of the disinfecting composition at 110° C. via the gravimetric method that will be described later.

Preferably, the residue content of the solution according to the present invention is less than 7 mg/kg (milligrams per kilogram of hydrogen peroxide solution), preferably less than 6 mg/kg, preferably less than 5 mg/kg, preferably less than 4 mg/kg, preferably less than 3 mg/kg and more preferentially less than 2 mg/kg. These residues may especially originate from the hydrogen peroxide stabilizer(s) and/or from compounds used in the manufacture of the hydrogen peroxide used in the present invention, for example an anticorrosion agent, a mineral acid or an additive known to those skilled in the art.

However, the content of stabilizer(s) initially present in the aqueous hydrogen peroxide solution is predominant to determine the content of dry residues finally present. Thus, the aim of the invention is to reduce or even to eliminate the presence of residues originating from the hydrogen peroxide stabilizer(s) used in the aqueous solution.

To do this, it is necessary for the stabilizer content to be less than 7 mg/kg, preferably less than 6 mg/kg, preferably less than 5 mg/kg, preferably less than 4 mg/kg, preferably less than 3 mg/kg, preferably less than 2.5 mg/kg and more preferentially less than 2 mg/kg.

In order to stabilize the hydrogen peroxide in the solution, the stabilizer content is preferably greater than 0.5 mg/kg, preferably greater than 1 mg/kg and more preferentially greater than 1.5 mg/kg. Advantageously, the stabilizer represents from 1 to 2.5 mg/kg by weight of the aqueous solution.

Thus, by means of the invention, it is possible to obtain an amount of dry residues of less than 2 mg/kg, but it is understood that, in order to obtain such a result, the choice of the hydrogen peroxide solution is essential, in other words said solution must comprise a very low level of dry residues derived from the manufacture of said peroxide, obviously less than 2 mg/kg.

According to a preferred embodiment of the invention, R or R' consists of a methyl group and the other R or R' consists of a substituted or unsubstituted methanoic acid (formic acid) group or a salt thereof. In this case, the stabilizer is methylglycinediacetic acid or a salt thereof.

According to another preferred embodiment of the invention, R or R' consists of a substituted or unsubstituted ethanoic acid (acetic acid) group or a salt thereof, and the other R or R' consists of a substituted or unsubstituted propanoic acid group or a salt thereof. In this case, the stabilizer is diacetic acid glutamate or a salt thereof.

Other characteristics or embodiments of the invention are presented below:
- advantageously, the aqueous solution according to the invention has a conductivity of 10 to 100 μS/cm (micro Siemens per centimetre), preferentially from 15 to 50 μS/cm and even more preferably from 20 to 40 μS/cm;
- advantageously, the aqueous solution according to the invention has a maximum acidity of 1 mmol/kg (millimoles per kilogram);
- advantageously, the loss of titer of said solution/stability of the hydrogen peroxide in the solution, measured according to the CEFIC-$H_2O_2$-AM-7161 method, is less than or equal to 5%, preferably less than or equal to 3% and preferably less than or equal to 2% relative to the initial concentration of hydrogen peroxide.

According to one possibility offered by the invention, the aqueous solution comprises, and preferably consists of
- from 20% to 50% of hydrogen peroxide,
- from 0.3 to 3 mg/kg and preferably from 0.5 to 7 mg/kg, by weight of the solution, of a stabilizer as defined above,
- optionally, from $1 \times 10^{-4}$% to $1 \times 10^{-2}$%, by weight of the solution, of additive(s),
- the remainder to 100% of water.

Advantageously, a disinfecting composition according to the invention constituted solely of water, hydrogen peroxide and the stabilizer according to the invention may be prepared. Surprisingly, this simple disinfecting composition proves to be efficient for preventing the decomposition of hydrogen peroxide when the disinfecting composition is contaminated with metallic impurities.

As the disinfecting composition according to the invention into has a very low content of dry evaporation residues (derived from the hydrogen peroxide stabilizer), it can withstand contamination with impurities without the total content of dry residues exceeding a maximum acceptable threshold imposed by the regulations in force concerning food packaging (at the present time set by the Food Chemical Codex).

The present invention also relates to the use of the aqueous solution as defined above for disinfecting/sterilizing a product.

Preferably, said product to be disinfected is chosen from the group constituted by packagings, premises, in particular hospital premises, and edible products, in particular fruit or vegetables.

Preferably, said packaging is chosen from the group constituted by a food packaging, such as a packaging for human or animal food, a packaging for a cosmetic product, a packaging for a pharmaceutical product and a packaging for a veterinary product.

Preferably, the disinfection/sterilization of said product is performed by spraying or vaporizing said solution onto said product.

The present invention also relates to the use of the aqueous solution as presented above for disinfecting/sterilizing a packaging by spraying the hydrogen peroxide solution described above or for the vapor disinfection of said hydrogen peroxide solution.

In the text hereinbelow, the stabilizer chosen from the family of substituted or unsubstituted aminopolycarboxylic acids (APCA), or salts thereof, of general formula:

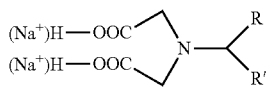

in which R and R' are chosen from the following functional groups:
C1 to C3 alkyls, preferably a methyl group,
C1 to C3 carboxylic acids,
will optionally be denoted by the term "stabilizer according to the invention" covering the abovementioned acids and the salts thereof.

The invention also relates to a process for disinfecting/sterilizing a product as defined above, in particular a packaging as defined above, characterized in that said product is placed in contact with the aqueous solution as described above.

Said placing in contact allows said product, preferably said packaging, to be disinfected/sterilized.

Preferably, said placing in contact is performed by spraying or vaporizing said solution onto said product, particularly preferably by spraying.

Advantageously, prior to being placed in contact with the stabilizer, the aqueous solution undergoes an operation intended to purify said solution, for instance distillation, one or more passes through ion-exchange resins, filtration or membrane techniques (microfiltration, ultrafiltration, nanofiltration) and/or reverse osmosis, the latter being preferred among the membrane techniques.

In the context of the present invention, passing the aqueous hydrogen peroxide solution through a preliminary purification operation may consist of one or more operations, i.e. including one or more purification techniques, especially those mentioned above, which are known to those skilled in the art.

The embodiments that will now be described relate especially both to the use of the disinfecting/sterilizing composition and to the disinfecting process according to the invention. These various embodiments may advantageously be combined.

DESCRIPTION OF EMBODIMENTS OF THE INVENTION

The invention is now described in greater detail and in a nonlimiting manner in the description that follows.

To manufacture an aqueous hydrogen peroxide solution according to the invention, hydrogen peroxide and the stabilizer according to the invention may be placed in contact by simple mixing. The stabilizer in solid form may in particular be dissolved in an aqueous hydrogen peroxide solution. The manufacture of hydrogen peroxide is a technique that is well known to those skilled in the art and does not constitute the subject of the present invention.

The present invention also relates to a process for manufacturing an aqueous hydrogen peroxide solution according to the present invention, comprising a step a) of mixing:
20 to 98%, preferably from 20 to 75%, preferably from 20% to 65%, preferably from 20 to 50% and more preferentially from 22% to 38%, by weight of the solution, of hydrogen peroxide, and
0.5 to 7 mg/kg, by weight of the solution, of a stabilizer as defined above.

Preferably, the mixing step allows dissolution of said stabilizer in the aqueous hydrogen peroxide solution.

Preferably, said process also comprises a step a'), prior to step a), of purifying said aqueous solution comprising hydrogen peroxide.

Parameters Measured and Methods Used

When reference is made to a standard method, the implementation conditions are those described in this method, unless an adaptation is explicitly mentioned.

The hydrogen peroxide titer in the disinfecting composition is measured according to the CEFIC-$H_2O_2$-AM-7157 method known to those skilled in the art. This method consists in titrating the hydrogen peroxide in an aqueous sulfuric acid solution using a standard volumetric solution of potassium permanganate.

The stability of the hydrogen peroxide is evaluated via the CEFIC-$H_2O_2$-AM-7161 method. This method consists in determining the percentage loss of hydrogen peroxide by measuring the hydrogen peroxide content before and after heating it at 96° C. for 16 hours.

The content of evaporation dry residues of the disinfecting composition is measured at 110° C. via the following gravimetric method:

1—A platinum capsule with a volume in the region of 300-350 mL (milliliters) is placed in a muffle furnace at 900° C. for one hour. The capsule is cooled in a desiccator and is weighed on a precision balance to an accuracy of 0.0001 g. This mass is noted as Y (in g).

2—An approximately 500 mL beaker is weighed to an accuracy of 0.0001 g (grams) and its mass is noted. About 300 g are added to this beaker. The beaker is weighed again to an accuracy of 0.0001 g. W1 (in grams) is noted as the difference between the mass of the beaker before and after the addition of the sample specimen.

3—The sample is gradually transferred into the platinum evaporation capsule (immersed in cold water) by means of a peristaltic pump making it possible to obtain a feed rate of about 75 g per hour. Once the test specimen has been transferred and the hydrogen peroxide has completely decomposed, the sample is evaporated to dryness on a water bath. Operations 2 and 3 are repeated twice so as to obtain a cumulative of sample specimens of between 750 and 1000 g. This makes it possible to obtain better precision on the determination of the dry residue.

4—The platinum capsule is then placed in a furnace at 110° C. for at least 1 hour.

5—The capsule is cooled in a desiccator for 30 minutes and is then weighed to an accuracy of 0.0001 g. This weight Z (in g) is noted.

6—The content of dry residue is calculated with the aid of the formula:

$$\text{Dry residue at } 110° \text{ C. (in g/kg)} = 1000 \times (Z-Y)/(W1+W2+W3)$$

in which
Z (in g) represents the mass of the capsule containing the dry residue after evaporation, Y (in g) represents the mass of the empty capsule,
W1, W2 and W3 (in g) represent the masses of the successive sample specimens.

EXAMPLES

The following examples illustrate the invention without limiting it. In particular, they reproduce the behavior of aqueous hydrogen peroxide solution is under working conditions, i.e. those of an aseptic packaging machine for sterilizing a packaging.

In all the examples presented below, it is considered that the amount of hydrogen peroxide in the aqueous solution is 35%. It should be noted that the stability is tested here for the pure aqueous solution and in the presence of a metallic contamination at low concentration (1 mg/liter of iron). In this last test, it will be accepted that the maximum threshold value is set at 20% in order to be in accordance with the invention.

The results for the amounts of dry residues include both those originating from the peroxide (i.e. derived essentially from its manufacture) and also those originating from the stabilizer(s), the latter residues being the only ones that the present invention intends to remove, or to reduce very significantly, from the (final) aqueous hydrogen peroxide solution.

The following starting materials are used:

Example 1

The aqueous solution of Example 1 comprises 0.1 mg/kg of methylglycinediacetic acid (or a salt thereof).

Example 2

The aqueous solution of Example 2 comprises 1.1 mg/kg of methylglycinediacetic acid (or a salt thereof).

Example 3

The aqueous solution of Example 3 comprises 3.3 mg/kg of methylglycinediacetic acid (or a salt thereof).

Example 4

The aqueous solution of Example 4 comprises 1.1 mg/kg of diacetic acid glutamate (or a salt thereof).

Example 5

(Comparative)
The aqueous solution of Example 5 is a grade of hydrogen peroxide currently marketed (Valsterane® 35S) available for applications for the disinfection of food packagings by spraying, comprising 4 mg/kg of a phosphonic acid as stabilizer.

Example 6

(Comparative)
The aqueous solution of Example 6 is a grade of hydrogen peroxide currently marketed (Valsterane® 35SB) available for applications for the disinfection of food packagings by spraying, comprising 16 mg/kg of a phosphonic acid as stabilizer.

Example 7

(Comparative)
The aqueous solution of Example 7 comprises 1.1 mg/kg of cyclohexanediaminotetraacetic acid (or a salt thereof).

Example 8

(Comparative)
The aqueous solution of Example 8 comprises 1.1 mg/kg of dipicolinic acid (or a salt thereof).

Example 9

(Comparative)
The aqueous solution of Example 9 comprises 1.1 mg/kg of diethylenetriaminepentaacetic acid (or a salt thereof).

Example 10

(in Accordance with the Invention, the Most Preferred Range)
The aqueous solution of Example 10 comprises 2.3 mg/kg of methylglycinediacetic acid (or a salt thereof).

Example 11

(in Accordance with the Invention, Preferred Range)
The aqueous solution of Example 11 comprises 4 mg/kg of methylglycinediacetic acid (or a salt thereof).

Example 12

(in Accordance with the Invention)
The aqueous solution of Example 12 comprises 6 mg/kg of methylglycinediacetic acid (or a salt thereof).

The results obtained are indicated in the table below:

| Ex. | Stability* (16 h/96° C.) | Dry residue at 110° C. (mg/kg) | Stability* under contamination conditions (1 mg/L of Fe) |
|---|---|---|---|
| 1 | 2.7 | 4 | 20 |
| 2 | 1.1 | 4.3 | 10 |
| 3 | 0.8 | 6.5 | 8 |
| 4 | 1.4 | 4.3 | 13 |
| 5 | 1 | 9 | 25 |
| 6 | 0.8 | 18 | 10 |
| 7 | 2 | 4.3 | 30 |
| 8 | 2.5 | 4.3 | 35 |
| 9 | 2 | 4.3 | 30 |
| 10 | 1 | 6 | 10 |
| 11 | 0.7 | 6.8 | 7 |
| 12 | 0.6 | 7 | 6 |

*expressed as a relative percentage loss of $H_2O_2$ titer

It is thus found that only the compositions according to the invention, in particular compositions 2 to 4, have excellent stability over time (with or without contamination) and an extremely low amount of dry residues.

The invention claimed is:
1. An aqueous hydrogen peroxide solution consisting of:
from 20 to 98%, by weight of the solution, of hydrogen peroxide,
from 0.5 to 7 mg/kg, by weight of the solution, of a stabilizer,
wherein the stabilizer is chosen from the family of substituted or unsubstituted aminopolycarboxylic acids (APCA), or salts thereof, of general formula:

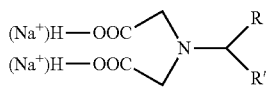

in which R and R' are selected from group consisting of the following functional groups:

C1 to C3 alkyls, and

C1 to C3 carboxylic acids, and the remainder to 100% of water.

2. The aqueous solution of claim 1, comprising from 20 to 75%, by weight of the solution, of hydrogen peroxide.

3. The aqueous solution of claim 1, wherein one of R or R' consists of a methyl group and the other of R or R' consists of a substituted or unsubstituted methanoic acid group or a salt thereof.

4. The aqueous solution of claim 1, wherein one of R or R' consists of a substituted or unsubstituted methanoic acid group or a salt thereof, and the other of R or R' consists of a substituted or unsubstituted propanoic acid group or a salt thereof.

5. The aqueous solution of claim 1, wherein the solution has a conductivity of 10 to 100 μS/cm.

6. The aqueous solution of claim 1, wherein the solution has a maximum acidity of 1 mmol/kg.

7. The aqueous solution of claim 1, wherein the solution has a content of dry residue at 110° C. of not more than 7 mg/kg.

8. The aqueous solution of claim 1, wherein the loss of titer of said solution, measured according to the CEFIC-$H_2O_2$-AM-7161 method, is less than or equal to 5% relative to the initial concentration of hydrogen peroxide.

9. A process for disinfecting/sterilizing a product, comprising placing the product in contact with the aqueous solution of claim 1.

10. The process of claim 9, wherein the placing in contact is performed by spraying or vaporizing said solution onto said product.

* * * * *